United States Patent
Shieh et al.

(10) Patent No.: US 9,949,929 B2
(45) Date of Patent: Apr. 24, 2018

(54) DRUG CARRIER AND MANUFACTURING METHOD THEREOF

(71) Applicant: National Taiwan University Hospital, Taipei (TW)

(72) Inventors: Ming-Jium Shieh, Taipei (TW); Cheng-Liang Peng, Taipei (TW); Yuan-I Chen, Taipei (TW)

(73) Assignee: NATIONAL TAIWAN UNIVERSITY HOSPITAL, Taipei (TW)

( * ) Notice: Subject to any disclaimer, the term of this patent is extended or adjusted under 35 U.S.C. 154(b) by 48 days.

(21) Appl. No.: 14/957,858

(22) Filed: Dec. 3, 2015

(65) Prior Publication Data
US 2017/0014344 A1    Jan. 19, 2017

(30) Foreign Application Priority Data
Jul. 13, 2015   (TW) .............................. 104122608 A (51) Int. Cl.
| | | |
|---|---|---|
| A61K 47/10 | (2017.01) | |
| A61K 31/704 | (2006.01) | |
| A61K 41/00 | (2006.01) | |
| A61K 47/22 | (2006.01) | |
| A61K 47/34 | (2017.01) | |
| A61K 9/107 | (2006.01) | |

(52) U.S. Cl.
CPC .......... *A61K 9/1075* (2013.01); *A61K 31/704* (2013.01); *A61K 41/0028* (2013.01); *A61K 41/0052* (2013.01); *A61K 47/10* (2013.01); *A61K 47/22* (2013.01); *A61K 47/34* (2013.01)

(58) Field of Classification Search
None
See application file for complete search history.

(56) References Cited

FOREIGN PATENT DOCUMENTS
WO    2009061473 A2    5/2009

OTHER PUBLICATIONS

Chen, Y., et al., "Traceable Self-Assembly of Laser-Triggered Cyanine-Based Micelle for Synergistic Therapeutic Effect", Adv. Healthcare Materials, 2015, pp. 1-11.*

Yan, Q.,et al., "Visible light-responsive micelles formed from dialkoxyanthracene-containing block copolymers", Chem Comm., 2012, pp. 1913-1915.*

Zhang, L., et al., "Fluorescent Micelles Based on Star Amphiphilic Copolymer with a Porphyrin Core for Bioimaging and Drug Delivery", Macromolecular Bioscience.*

Yoon, K., et al., "Amphiphilic poly(ethylene glycol)-poly(ε-caprolactone) AB2 miktoarm copolymers for self-assembled nanocarrier systems: synthesis, characterization, and effects of morphology on antitumor activity", Polymer Chemistry, pp. 531-542.*

Gorka, A.P., et al., "A Near-IR Uncaging Strategy Based on Cyanine Photochemistry", JACS, 2014, pp. 14153-14159.*

James, N.S., et al., "Evaluation of Polymethine Dyes as Potential Probes for Near Infrared Fluorescence Imaging of Tumors: Part-1", Theranostics, 2013, pp. 692-702.*

Guo, "Dual imaging-guided photothermal/photodynamic therapy using micelles", Biomaterials, 2014, pp. 4656-4666.*

Moon Suk Kim et al., "Preparation of methoxy poly(ethyleneglycol)-blockpoly( caprolactone) via activated monomer mechanism and examination of micellar characterization", Polymer Bulletin, vol. 55, 2005, pp. 149-156.

Jae Min Oh et al., "Ring-opening polymerization of epsilon-caprolactone by poly(propyleneglycol) in the presence of a monomer activator", Polymer, vol. 50, 2009, pp. 6019-6023.

Liang Cheng et al., "PEGylated Micelle Nanoparticles Encapsulating a Non-Fluorescent Near-Infrared Organic Dye as a Safe and Highly-Effective Photothermal Agent for In Vivo Cancer Therapy", Adv. Funct. Mater., vol. 23, 2013, pp. 5893-5902.

Intellectual Property Office, Ministry of Economic Affairs, R. O. C, "Office Action", dated Nov. 30, 2016, Taiwan.

Davide Brambilla et al., Design of fluorescently tagged poly(alkyl cyanoacrylate) nanoparticles for human brain cell imaging. Chem. Commun., 2010, 46, 2602-2604, Full Text.

* cited by examiner

*Primary Examiner* — Michael G Hartley
*Assistant Examiner* — Lance W Rider
(74) *Attorney, Agent, or Firm* — Locke Lord LLP; Tim Tingkang Xia, Esq.

(57) ABSTRACT

A drug carrier and a manufacturing method thereof are provided. The drug carrier includes a hydrophilic group, a hydrophobic group and an organic dye. The hydrophilic group and the hydrophobic group are connected by the organic dye. A plurality of the drug carriers are self-assemblable in a polar solvent to form a nanomicelle. The hydrophilic groups are located at the outer region of the nanomicelle, and the hydrophobic groups are located at the inner region of the nanomicelle.

11 Claims, 8 Drawing Sheets

DRUG CARRIER AND MANUFACTURING METHOD THEREOF

CROSS-REFERENCE TO RELATED APPLICATIONS

This non-provisional application claims priority under 35 U.S.C. § 119(a) on Patent Application No(s). 104122608 filed in Taiwan, R.O.C. on Jul. 13, 2015, the entire contents of which are hereby incorporated by reference.

TECHNICAL FIELD

The disclosure relates to a drug carrier and a manufacturing method thereof, more particularly to a drug carrier which is able to form a nanomicelle in a polar solvent by self-assembly and a manufacturing method thereof.

BACKGROUND

The tumor is formed by abnormal growing tissues, and these tissues are consisted of cancer cells. In order to collect sufficient nutrition for cell growth, a large number of blood vessels spread in the tumor for providing nutrition to cancer cells. These blood vessels have thin vascular walls so that the plasma with nutrition can easily penetrate the vascular walls and enter the intercellular space. In addition, the lymphatic drainage efficiency in the tumor is poor so that most of the nutrition is retained in the intercellular space for cancer cell growth. The uncontrollable increase of the cancer cell number may have negative influence on normal tissues, organs or even bring life threatening. With the ranking up of cancer in the top ten cause of death, the cancer therapy research becomes more important.

SUMMARY

According to the present disclosure, a drug carrier includes a hydrophilic group, a hydrophobic group and an organic dye. The hydrophilic group and the hydrophobic group are connected by the organic dye. A plurality of the drug carriers are self-assemblable to form a nanomicelle in a polar solvent. The hydrophilic groups are located at the outer region of the nanomicelle, and the hydrophobic groups are located at the inner region of the nanomicelle.

According to the present disclosure, a method of manufacturing a drug carrier includes the following steps. Provide a first mixture, wherein the first mixture comprises a hydrophilic polymer, an organic dye and a hydrophilic organic solvent, and the hydrophilic polymer comprises a hydrophilic group. Stir the first mixture at a first temperature to obtain a first composite by a substitution reaction, wherein the first composite comprises the hydrophilic group and the organic dye which are connected with each other. Obtain a second mixture, wherein the second mixture comprises the first composite, a hydrophobic polymer and a hydrophobic organic solvent, and the hydrophobic polymer comprises a hydrophobic group. Stir the second mixture at a second temperature to obtain a drug carrier by a polymerization reaction, wherein the drug carrier comprises the hydrophilic group, the organic dye and the hydrophobic group, and the hydrophilic group and the hydrophobic group are connected by the organic dye. A plurality of the drug carriers are self-assemblable to form a nanomicelle in a polar solvent. The hydrophilic groups are located at the outer region of the nanomicelle, and the hydrophobic groups are located at the inner region of the nanomicelle.

BRIEF DESCRIPTION OF THE DRAWINGS

The present disclosure will become better understood from the detailed description given hereinbelow and the accompanying drawings which are given by way of illustration only and thus are not limitative of the present application and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figure 1A:
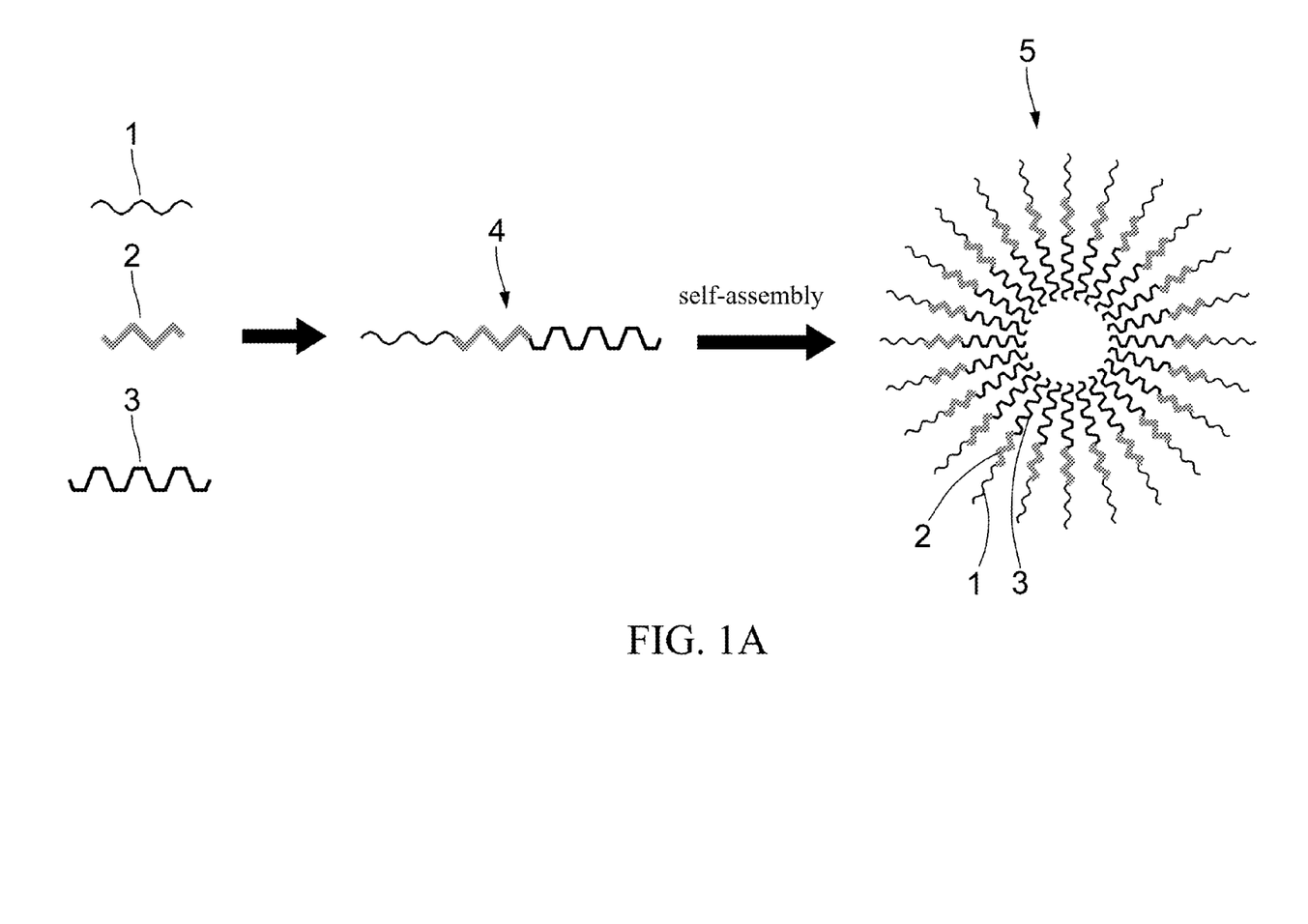
FIG. 1A is a schematic view of a drug carrier and a nanomicelle assembled by the drug carriers according to an embodiment of the disclosure.
Figure 1B:
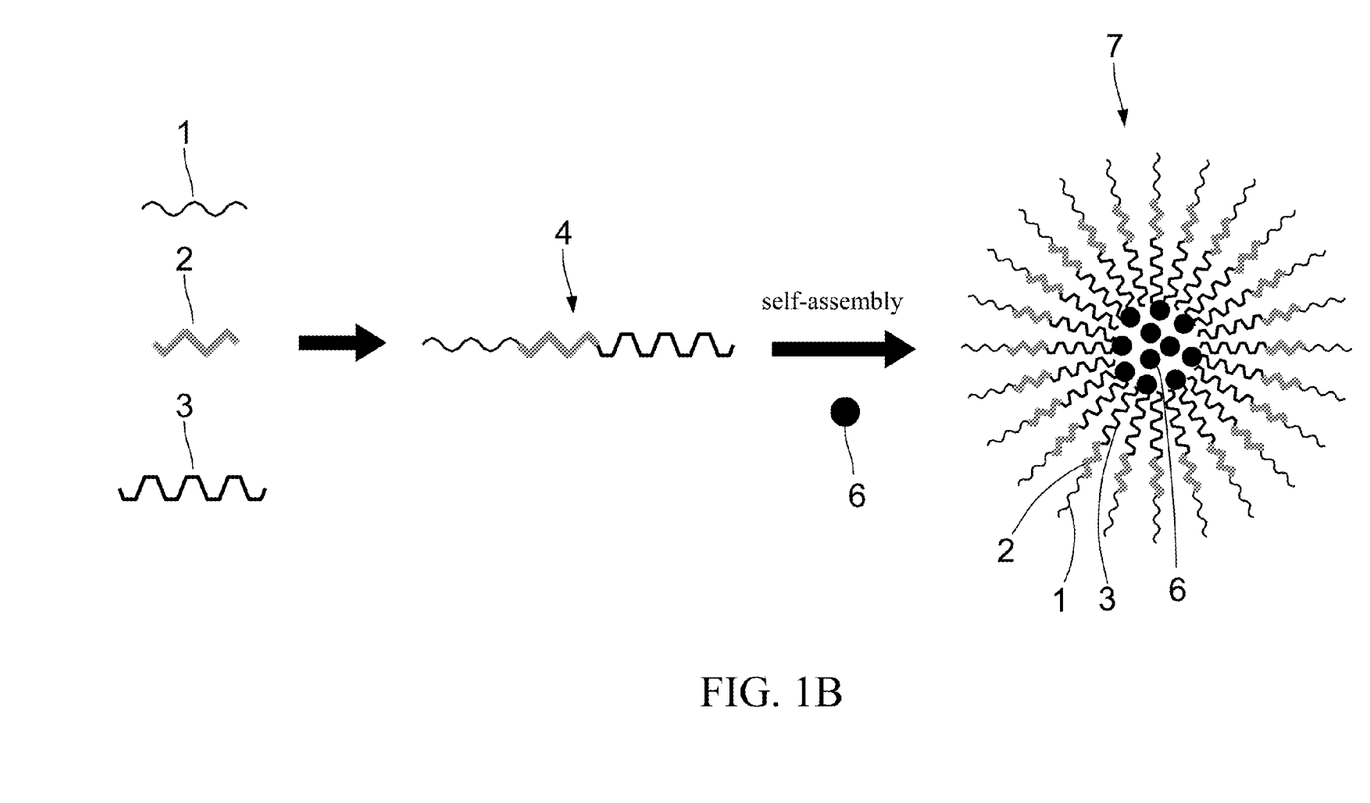
FIG. 1B is a schematic view of the drug carrier and the nanomicelle, which encapsulating drug molecules, assembled by the drug carriers according to the embodiment of the disclosure.
Figure 2:
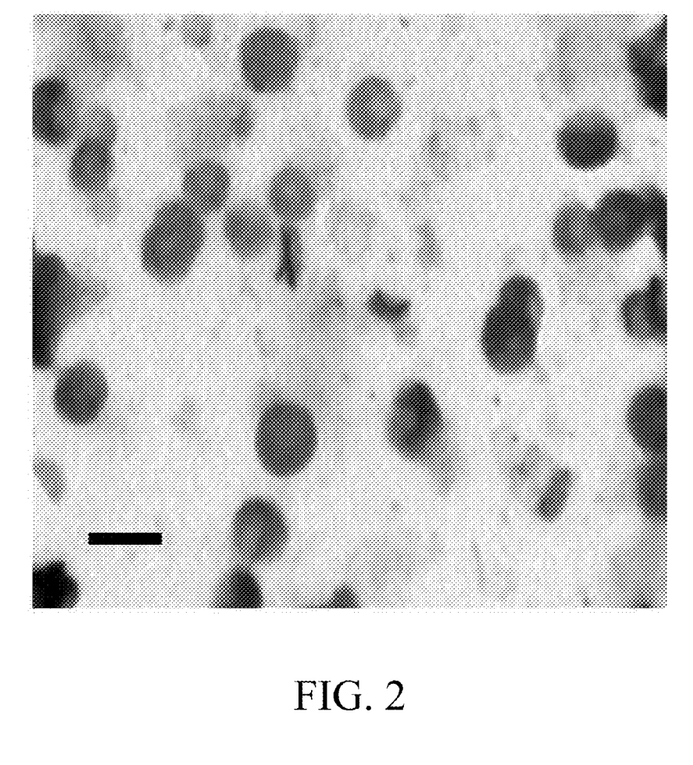
FIG. 2 is an electron microscope photograph of the nanomicelle according to the embodiment of the disclosure.

Structures of a drug carrier and a nanomicelle constructed by self-assembly of the drug carriers according to an embodiment of the present disclosure are introduced hereafter. Please refer to FIG. 1A, FIG. 1B and FIG. 2. FIG. 1A is a schematic view of a drug carrier and a nanomicelle assembled by the drug carriers according to an embodiment of the disclosure. FIG. 1B is a schematic view of the drug carrier and the nanomicelle, which encapsulating drug molecules, assembled by the drug carriers according to the embodiment of the disclosure. FIG. 2 is an electron microscope photograph of the nanomicelle according to the embodiment of the disclosure.

The drug carrier 4 includes a hydrophilic group 1, an organic dye 2 and a hydrophobic group 3. The organic dye 2 connects the hydrophilic group 1 and the hydrophobic group 3 so that the drug carrier 4 is an amphiphilic molecule which is hydrophilic and hydrophobic at the same time.

The hydrophilic group 1 is a hydrophilic part in a hydrophilic polymer. The hydrophilic polymer, for example, includes methoxy poly(ethylene glycol) (mPEG), poly(ethylene glycol) (PEG), poly(ethylene glycol)-thiol (PEG-SH), poly(ethylene glycol)-amine (PEG-NH$_2$), poly(2-ethyl-2-oxazoline) (PEO$_z$), polyethylenimine (PEI), poly(acrylic acid) (PAA) or polypropylene glycol) (PPG). The organic dye 2 can include 3,5-diphenyl-aza-BODIPY, 3,5-dimethyl-BODIPY, amine-heptamethylcyanine dye, indocyanine Green (ICG), merocyanine, tricarbocyanine dye, Cyanine 5, Cyanine 7, MHI-148, American Dye Source 780 (ADS780), IR-780 iodide, heptamethine carbocyanin, IR-783, IR-808, IR-820, xanthene dyes, squaraines, bis(vinyl ruthenium)-modified Squaraine dyes, hydrophilic porphyrin (THPP), Zn-THPP or photofrin.

Both the 3,5-diphenyl-aza-BODIPY and the 3,5-dimethyl-BODIPY are BODIPY dyes. The BODIPY is a derivative of boron-dipyrromethene. The amine-heptamethylcyanine dye, the indocyanine Green (ICG), the merocyanine, the tricarbocyanine dye, the Cyanine 5, the Cyanine 7, the MHI-148, the American Dye Source 780 (ADS780), the IR-780 Iodide, the heptamethine carbocyanine, the IR-783, the IR-808 and the IR-820 are cyanine dyes. The xanthene dyes is rhodamines. The squaraines and the bis(vinyl ruthenium)-modified squaraine dyes are squaraines. The hydrophilic Porphyrin (THPP), the Zn-THPP and the photofrin are phthalocyanines and porphyrin derivatives. In this embodiment, the organic dye 2 is hydrophobic. However, the disclosure is not limited to the hydrophilicity and the hydrophobicity of the organic dye. In other embodiment, the organic dye can be hydrophilic.

The hydrophobic group 3 is a hydrophobic part in the hydrophobic polymer. The hydrophobic hydrophobic polymer, for example, includes poly(ε-caprolactone) (PCL), polylactide) (PLA), poly(D-lactic acid) (PDLA), poly(L-lactic acid) (PLLA), poly(lactic-co-glycolic acid) (PLGA) or poly(glycolic acid) (PGA).

In this embodiment, the organic dye 2 in the drug carrier 4 connects one hydrophilic group 1 and two hydrophobic groups 3 by covalent bond, and the drug carrier 4 can be represented by formula (I).

(I)

In the formula (I), A is the hydrophilic group 1, B is the hydrophobic group 3 and C is the organic dye 2. However, the disclosure is not limited to the number of the hydrophilic group or the hydrophobic group connected to the organic dye. In other embodiments, one organic dye can connect one hydrophilic group and one hydrophobic group by covalent bond, or one organic dye can connect more than two hydrophilic groups and more than one hydrophobic groups. In still other embodiments, two organic dyes, which are directly connected with each other by covalent bond, can respectively connect one hydrophilic group and one hydrophobic group by covalent bond.

In this embodiment, a part of the hydrophilic group 1 close to the organic dye 2 and a part of the hydrophobic group 3 close to the organic dye 2 are not directly connected to each other by covalent bond. However, the disclosure is not limited to the bond relation between the hydrophilic group and the hydrophobic group. In other embodiments, the part of the hydrophilic group close to the organic dye and the part of the hydrophobic group close to the organic dye are directly connected to each other by covalent bond.

As shown in FIG. 1A and FIG. 2, each of the drug carriers 4 having the hydrophilic group and the hydrophobic group is amphiphilic. When a plurality of amphiphilic drug carriers 4 are in a polar solvent such as dimethyl sulfoxide, the drug carriers 4 can form a nanomicelle 5 by self-assembly in a polar solvent. In detail, the hydrophobic groups 3 of the drug carriers 4 in the polar solvent such as the dimethyl sulfoxide are repulsed by the polar molecules of the polar solvent so that the drug carriers 4 assemble the nanomicelle 5 having a spherical structure spontaneously and orderly. The nanomicelle 5 is a single layer structure in this embodiment but not limited thereto. In other embodiments, the nanomicelle can be a double-layer structure which is similar to a nanoliposome. Therefore, the volume of the hydrophobic groups 3 in the drug carriers 4 which form the nanomicelle 5 is reduced so as to minimize the repulsion force applied on the hydrophobic groups 3.

The hydrophilic groups 1 of the drug carriers 4 are located at an outer area of the nanomicelle 5 and close to the polar solvent such as the dimethyl sulfoxide. The hydrophobic groups 3 thereof are located at a center area of the nanomicelle 5. The organic dyes 2 thereof are located between an area of the nanomicelle 5 between the hydrophilic groups 1 and the hydrophobic groups 3. As a result, when the organic dye 2 is hydrophobic, the hydrophobic organic dyes 2 inside the nanomicelle 5 are dissolvable in the polar solvent with the help of the hydrophilic groups 1. In this embodiment, the drug carriers 4 form the nanomicelle in dimethyl sulfoxide by self-assembly, and the nanomicelle can be dissolved in dimethyl sulfoxide. However, the disclosure is not limited to the kind of the polar solvent where the nanomicelle dissolved. In other embodiments, the drug carriers can form nanomicelles in water, water solution, other kind of polar solvent and other kind of polar solution by self-assembly, and the nanomicelles can be dissolved in water, water solution, other kind of polar solvent and other kind of polar solution.

According to the search results in medical science, when a diameter of a water-soluble substance is less than 300 nanometers (nm), the water-soluble substance is capable for penetrating the vascular walls and entering the intercellular space between cancer cells. Moreover, when the diameter of a water-soluble substance is less than 200 nm, it is easier for the water-soluble substance to penetrate the vascular walls and enter the intercellular space between cancer cells. Then the cancer cells are capable of ingesting the water-soluble substance at the intercellular space into themselves by endocytosis. In this embodiment, a diameter of the nanomicelles 5 is from 110 nm to 130 nm so that the nanomicelles 5 are capable for penetrating the vascular walls, entering the intercellular space and being ingested by the cancer cells to complete drug transportation. However, the disclosure is not limited to the size of the nanomicelle. In some embodiments, the diameter of the nanomicelle is from 80 nm to 200 nm. In other embodiments, the diameter of the spherical nanostructure is from 20 nm to 300 nm.

When the nanomicelles formed by the drug carriers are irradiated by a near-infrared (NIR) light, the organic dyes in the drug carriers emit fluorescence for generating a fluorescence image. As a result, when the nanomicelles inside a living body (for example, human body) are irradiated by the near-infrared light, the fluorescence emitted by the organic dyes can be used for observing the distribution of the nanomicelles in the living body. When the nanomicelles are used in cancer therapies, the location of the tumor can be determined by the fluorescence image. An area in the fluorescence image showing intense fluorescence distribution is the area where the tumor locates because the nanomicelles are easier to penetrate through the blood vessels in the tumor and be retained in the tumor. In this embodiment, the organic dyes 2 in the nanomicelles 5 are capable for absorbing the light with a wavelength from 400 nm to 1000 nm and then emitting the fluorescence with the wavelength from 650 nm to 850 nm. However, the disclosure is not limited to the wavelength which the organic dyes absorb and emit. In other embodiments, the organic dyes in the drug carriers can absorb the light with a wavelength from 500 nm to 800 nm and then emitting the fluorescence with the wavelength from 650 nm to 850 nm.

Moreover, when the nanomicelles formed by the drug carriers are irradiated by the near-infrared light, the organic dyes in the nanomicelles absorb the energy of the near-infrared light so that the temperatures of the nanomicelles are raised to a photothermal therapy temperature for executing a photothermal therapy. The photothermal therapy is that a photosensitizer is irradiated by a light with specific wavelength and then absorbs the energy of the light so as to release heat for destroying target cells. The photothermal therapy temperature is a temperature which causes irrecoverable damage on the physiological functions of cells. For executing the photothermal therapy on cancer cells, the photothermal therapy temperature is preferably over 43 Celsius degrees (° C.). The heat generated from the vibrations of the organic dyes, which absorb the light energy as the photosensitizer, raises the temperature of the nanomicelle to the photothermal therapy temperature.

As a result, when the nanomicelles are used in cancer therapies, the organic dyes are irradiated by near-infrared light so as to generate heat to raise the temperature of the nanomicelles to or over the photothermal therapy temperature, and thereby causing irrecoverable damage on the cancer cells. Therefore, physiological functions of the cancer cells are irrecoverably damaged by heat so that the cancer cells are killed. In this embodiment, after irradiating by a near-infrared light for one minute, the temperature of the nanomicelles 5 is raised to over 50.4° C. However, the disclosure is not limited to a heat generation ability of the nanomicelle. In other embodiments, after irradiating by a near-infrared light for one minute, the temperature of the nanomicelles can be raised to over 43° C.

As shown in FIG. 1B, when the drug carriers 4 and a plurality of drug molecules 6 are located in a polar solvent such as dimethyl sulfoxide, the drug carriers 4 form the nanomicelle by self-assembly and surround the drug molecules 6. as a drug-encapsulating nanomicelle 7. As a result, when circulating in the blood vessels, the drug molecules 6 are encapsulated in the drug-encapsulating nanomicelles 7 without directly contacting the normal cells. Once the drug-encapsulating nanomicelles 7 are gathered in the tumor through the blood circulation, high dose of the drug molecules 6 are released from the drug-encapsulating nanomicelles 7, and therefore the drug molecules 6 can directly apply to the cancer cells in the tumor. Accordingly, damages on normal cells caused by high dose of the drug molecules during the cancer therapy are prevented so that burden of the patient's body is reduced. In addition, even though the drug molecules 6 are hydrophobic, the hydrophobic drug molecules 6 are capable of being uniformly dispersed in water as being encapsulated in the drug-encapsulating nanomicelles 7; therefore, the hydrophobic drug molecules 6 can be absorbed easily to enter blood vessels and the blood vessels fluently to enter the tumor. The drug molecule can generate unrecoverable damage on the cancer cell to kill the cancer cell. The drug molecule, for example, includes Doxorubicin (Doxo), 7-ethyl-10-hydroxycamptothecin (SN-38), Camptothecin (CPT), Paclitaxel, 17-(Allylamino)-17-demethoxygeldanamycin (17-AAG), Celecoxib, Capecitabine, Docetaxel, Epothilone B, Erlotinib, Etoposide, GDC-0941, Gefitinib, Geldanamycin, Imatinib, Intedanib, Lapatinib, Neratinib, NVP-AUY922, NVP-BEZ235, Panobinostat), Pazopanib, Ruxolitinib, Saracatinib, Selumetinib, Sorafenib, Sunitinib, Tandutinib, Temsirolimus, Tipifarnib, Tivozanib, Topotecan, Tozasertib, Vandetanib, Vatalanib, Vemurafenib, Vinorelbine, Vismodegib, Vorinostat or ZSTK474. In this embodiment, the drug molecule 6 is hydrophobic. However, the drug molecule can be hydrophilic in other embodiments.

In this embodiment, the drug carriers 4 and the drug molecules 6 form the drug-encapsulating nanomicelles 7 together in the dimethyl sulfoxide. However, the disclosure is not limited to the polar solvent which the plurality of drug carriers and the plurality of drug molecules in. In other embodiments, the drug-encapsulating nanomicelles can be formed in water, water solution, other kind of polar solvent and other kind of polar solution by self-assembly. A diameter of the drug-encapsulating nanomicelles 7 can be from 110 nm to 160 nm. When the diameter of the drug-encapsulating nanomicelles 7 is less than 300 nm, the drug-encapsulating nanomicelles 7 are capable of penetrating the blood vessels to the intercellular space of the cancer cells and being ingested into the cancer cells by endocytosis to execute cancer therapy. When the diameter of the drug-encapsulating nanomicelles 7 is less than 200 nm, the drug-encapsulating nanomicelles 7 can penetrate the blood vessels more fluently. When the diameter of the drug-encapsulating nanomicelles 7 is larger than 20 nm, a concentration of the drug molecule 6 in the drug-encapsulating nanomicelles 7 is high enough for damaging the cancer cells. When the diameter of the drug-encapsulating nanomicelles 7 is larger than 80 nm, the concentration of the drug molecule 6 in the drug-encapsulating nanomicelles 7 is high enough for irrecoverably damaging the cancer cells and obtaining better cancer therapy result.

In this embodiment, the diameter of the drug-encapsulating nanomicelles 7 is from 110 nm to 160 nm. However, the disclosure is not limited to the diameter of the drug-encapsulating nanomicelles. In some embodiments of the disclosure, the diameter of the drug-encapsulating nanomicelles is from 80 nm to 200 nm. In other embodiments of the disclosure, the diameter of the drug-encapsulating nanomicelles is from 20 nm to 300 nm.

In this embodiment, the drug carriers 4 encapsulate the drug molecules 6 by self-assembly to form the drug-encapsulating nanomicelle 7. However, the disclosure is not limited to the number of the drug molecules encapsulated in one drug-encapsulating nanomicellespherical nanostructure. In other embodiments, there can be only one drug molecule in each of the drug-encapsulating nanomicelles.

Figure 3A:
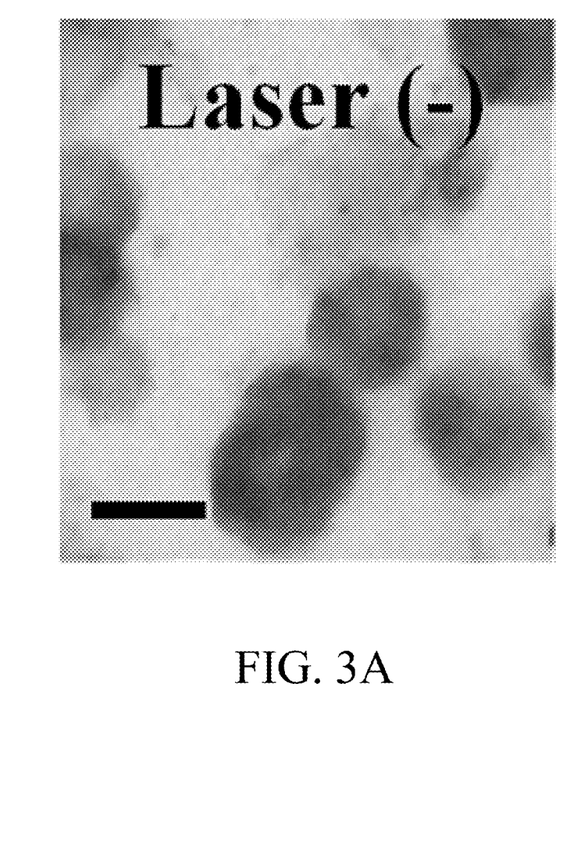
FIG. 3A is an electron microscope photograph of the drug-encapsulating nanomicelle before irradiated by near-infrared laser according to the embodiment of the disclosure.
Figure 3B:
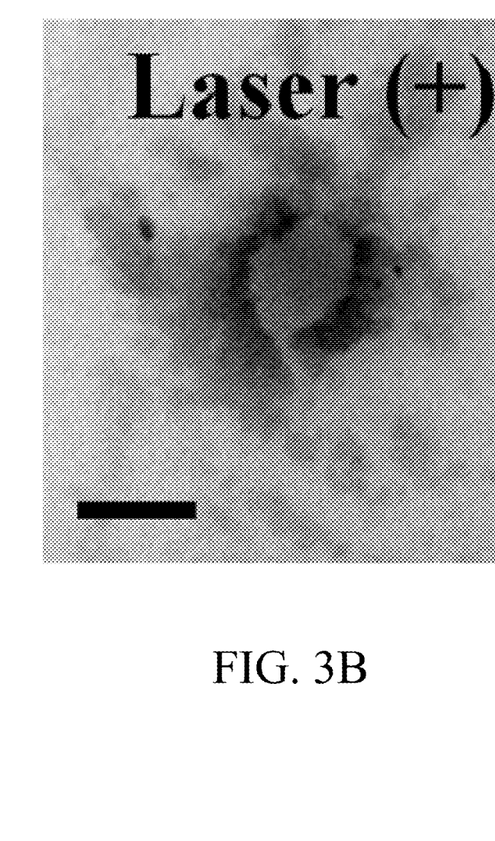
FIG. 3B is an electron microscope photograph of the drug-encapsulating nanomicelle after irradiated by near-infrared laser according to the embodiment of the disclosure.

Please refer to FIG. 3A and FIG. 3B. FIG. 3A is an electron microscope photograph of the drug-encapsulating nanomicells before irradiated by near-infrared laser according to the embodiment of the disclosure. FIG. 3B is an electron microscope photograph of the drug-encapsulating nanomicelle after irradiated by near-infrared laser according to the embodiment of the disclosure The drug-encapsulating nanomicelles, as shown in FIG. 3A, have spherical structure before irradiated by near-infrared laser. Once the drug-encapsulating nanomicelles are irradiated by the near-infrared (NIR) light, the organic dyes in the drug carriers absorb the energy of the near-infrared light so that the drug-encapsulating nanomicelles become unstable and ruptured. As shown in FIG. 3B, the drug-encapsulating nanomicelles break into pieces after irradiated by near-infrared laser, and therefore the drug molecules are released from the drug-encapsulating nanomicelles.

Accordingly, when the drug-encapsulating nanomicelles are used in cancer therapy, first, the drug-encapsulating nanomicelles are administered into living body, for example, orally or by injection. Next, after the drug-encapsulating nanomicelles are moved and accumulated in the tumor, the location of the tumor is irradiated by the near-infrared light. Therefore, the organic dyes of the drug-encapsulating nanomicelles in the tumor emit fluorescence, and an aggregation of the drug-encapsulating nanomicelles in the tumor can be confirmed by the fluorescence image. At the same time, the drug molecules are released from the drug-encapsulating nanomicelles and damage the cancer cells to kill the cancer cells. Moreover, the organic dyes absorb the near-infrared light, and then the temperature of the drug-encapsulating nanomicelles as well as the cancer cells are raised to a photothermal therapy temperature so as to irrecoverably damage and kill the cancer cells. As a result, the drug molecules released by the drug-encapsulating nanomicelles in the tumor and the heat released by the organic dyes for executing photothermal therapy together generate the synergistic therapeutic effect; therefore, the number of survive cancer cells after the cancer therapy by the drug-encapsulating nanomicelles is greatly reduced.

Figure 4:
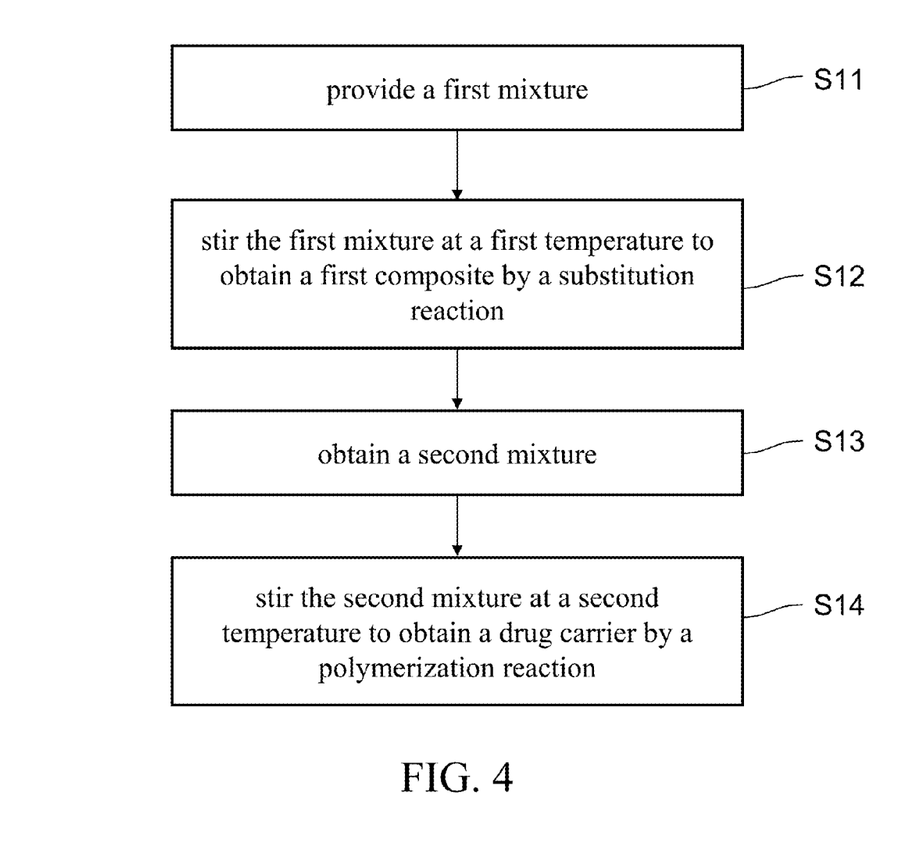
FIG. 4 is a schematic view of a manufacturing process of the drug carrier according to the embodiment of the disclosure.

The manufacturing method of the drug carrier is introduced in the following paragraph. Please refer to FIG. 4. FIG. 4 is a schematic view of a manufacturing process of the drug carrier according to the embodiment of the disclosure.

First, provide a first mixture (S11). In detail, the first mixture includes hydrophilic polymers, organic dyes and a hydrophilic organic solvent, and the hydrophilic polymers, the organic dyes and the hydrophilic organic solvent are mixed in a container to obtain the first mixture. Each of the hydrophilic polymers includes at least one hydrophilic group. The hydrophilic polymers, for example, includes methoxy poly(ethylene glycol) (mPEG), poly(ethylene glycol) (PEG), poly(ethylene glycol)-thiol (PEG-SH), poly (ethylene glycol)-amine (PEG-NH$_2$), poly(2-ethyl-2-oxazoline) (PEO$_Z$), polyethylenimine (PEI), poly(acrylic acid) (PAA) or polypropylene glycol) (PPG). The organic dyes, for example, includes 3,5-diphenyl-aza-BODIPY, 3,5-dimethyl-BODIPY, amine-heptamethylcyanine dye, indocyanine Green (ICG), merocyanine, tricarbocyanine dye, Cyanine 5, Cyanine 7, MHI-148, American Dye Source 780 (ADS780), IR-780 iodide, heptamethine carbocyanin, IR-783, IR-808, IR-820, xanthene dyes, squaraines, bis (vinyl ruthenium)-modified Squaraine dyes, hydrophilic porphyrin (THPP), Zn-THPP or photofrin. The hydrophilic organic solvent, for example, is dimethylformamide (DMF). When the organic dyes are hydrophobic, solubilizing agents such as triethanolamine (TEA) can be added into the first mixture so as to help the hydrophobic organic dyes to be dissolved in the hydrophilic organic solvent.

Next, stir the first mixture at a first temperature to obtain a first composite by a substitution reaction (S12). In detail, the first mixture, which is at the first temperature, is stirred under an anoxia atmosphere, and therefore, the hydrophilic polymers and the organic dyes in the first mixture undergo the substitution reaction to obtain a first solution including the first composites. The substitution reaction, for example, is a meso-chloride replacement reaction. The first composite includes a hydrophilic group and the organic dye. The organic dye is connected to the hydrophilic group by a covalent bonding. The first temperature is a reaction temperature of the substitution reaction between the hydrophilic polymer and the organic dye. A yield of the first composites is increased when the hydrophilic polymers and the organic dyes undergo the substitution reaction at the first temperature. The anoxia atmosphere, for example, is nitrogen atmosphere. The first composite in the first solution can be purified by dialysis so that a concentration of the first composite is increased. Then the solvent in the first solution is removed by lyophilization so as to obtain dried first composites.

In this embodiment, the first temperature is from 65° C. to 100° C. However, the disclosure is not limited to the first temperature. In other embodiments, the first temperature is determined by the hydrophilic polymer and the organic dye for increasing the yield of the first composite. In this embodiment, the anoxia atmosphere is a nitrogen atmosphere. However, the disclosure is not limited to the kind of the anoxia atmosphere. In other embodiments, the anoxia atmosphere can be an argon atmosphere or a helium atmosphere.

Next, obtain a second mixture (S13). In detail, the second mixture includes the first composite, hydrophobic polymers, a hydrophobic solvent and a catalyst which are all located in a container. The hydrophobic polymer includes at least one hydrophobic group. The hydrophobic polymer, for example, includes poly(ε-caprolactone) (PCL), poly(L-lactide) (PLA), poly(D-lactic acid (PDLA), poly(L-lactic acid) (PLLA), poly(lactic-co-glycolic acid) (PLGA) or poly(glycolic acid) (PGA). The hydrophobic organic solvent, for example, is dichloromethane (DCM). The catalyst, for example, is HCl in Ether, Sn(OCt)$_2$ or other kind of catalysts which can facilitate the polymerization reaction of the first composite and the hydrophobic polymer.

In this embodiment, the catalyst is added in the second mixture, but the disclosure is not limited thereto. In other embodiments, there can be no catalyst in the second mixture.

Last, stir the second mixture at a second temperature to obtain a drug carrier by a polymerization reaction (S14). In detail, the second mixture, which is at the second temperature, is stirred under an anoxia atmosphere, and therefore the first composites and the hydrophobic polymers in the second mixture undergo the polymerization reaction to obtain a second solution including the drug carriers. The polymerization reaction, for example, is ring-opening polymerization. Each of the drug carriers includes the first composite and the hydrophobic group. The organic dye in the first composite is connected to the hydrophobic group by a covalent bonding. The second temperature is a reaction temperature of the polymerization reaction between the first composite and the hydrophobic group. A yield of the drug carrier is increased when the first composites and the hydrophobic groups undergo the polymerization reaction at the second temperature. The anoxia atmosphere, for example, is a nitrogen atmosphere. The drug carriers in the second solution can be purified by dialysis so that a concentration of the drug carrier is increased. Then the solvent in the second solution is removed by lyophilization so as to obtain dried drug carriers.

In this embodiment, when the catalyst is HCl in Ether, the second temperature is from 25° C. to 40° C. However, the disclosure is not limited to the catalyst and the second temperature determined by the catalyst. In some embodiments, the catalyst can be Sn(OCt)$_2$, and the second temperature can be from 110° C. to 150° C. In some embodiments, the catalyst is determined by the first composite and the hydrophobic polymer for increasing the yield of the drug carrier. In other embodiments, there can be no catalyst in the second mixture, and the second temperature is determined by the first composite and the hydrophobic polymer. In this embodiment, the anoxia atmosphere is a nitrogen atmosphere. However, the disclosure is not limited to the kind of the anoxia atmosphere. In other embodiments, the anoxia atmosphere can be an argon atmosphere or a helium atmosphere.

When manufacturing nanomicelles by the drug carriers, the dried drug carriers are uniformly dissolved in dimethyl sulfoxide (DMSO) to obtain a drug-carrier-DMSO solution. The drug carriers form nanomicelles with spherical structure in the drug-carrier-DMSO solution by self-assembly. Next, the dimethyl sulfoxide in the drug-carrier-DMSO solution is removed by lyophilization so as to obtain the nanomicelles. In this embodiment, the drug carriers form nanomicelles in the drug-carrier-DMSO solution by self-assembly. However, the disclosure is not limited to the solvent which the drug carriers dissolved in. In other embodiments, the drug carriers can form nnomicelles in water, water solution, other polar solvents or other polar solutions by self-assembly.

When manufacturing drug-encapsulating nanomicelles by the drug carriers and drug molecules, first, the dried drug carriers and the drug molecules are uniformly dissolved in dimethyl sulfoxide (DMSO) to obtain a drug-carrier-drug-molecule-DMSO solution. The drug carriers surround the drug molecules and form the drug-encapsulating nanomicelles with spherical structure in the drug-carrier-drug-molecule-DMSO solution by self-assembly. Next, the dimethyl sulfoxide in the drug-carrier-drug-molecule-DMSO solution is removed by lyophilization so as to obtain a mixture of the drug-encapsulating nanomicelles and crystals of the drug molecules which are not encapsulated in the drug-encapsulating nanomicelles. Last, the drug-encapsulating nanomicelles and the crystals of the drug molecules in the mixture are separated by a sterile filter to obtain the drug-encapsulating nanomicelles.

The sterile filter for separating the drug-encapsulating nanomicelles and the crystals of the drug molecules which are not encapsulated in the drug-encapsulating nanomicelles has the mesh size between a diameter of the drug-encapsulating nanomicelle and a diameter of the crystal of the drug molecules which are not encapsulated in the drug-encapsulating nanomicelle. Therefore, the drug-encapsulating nanomicelles and the crystals of the drug molecules which are not encapsulated in the drug-encapsulating nanomicelles can be separated by the sterile filter. In this embodiment, the drug carriers and the drug molecules form the drug-encapsulating nanomicelles in the dimethyl sulfoxide solution by self-assembly. However, the disclosure is not limited to the solvent which the drug carriers and the drug molecules are dissolved in. In other embodiments, the drug carriers and the drug molecules can form the drug-encapsulating nanomicelles in water, water solution, other polar solvents or other polar solutions by self-assembly.

The following descriptions are two embodiments about the drug carriers and the manufacturing process thereof in the present disclosure. The effort of the drug carriers in the two embodiments are tested by experiments so as to certify the effort of the drug carriers used in cancer therapies.

Example 1

First, 1 gram (g) of methoxy poly(ethylene glycol) (mPEG), 256 milligrams (mg) of amine-heptamethylcyanine dye, 15 milliliters (ml) of dimethylformamide (DMF) and 125 microliters (μl) of triethanolamine (TEA) are mixed in a container to obtain a first mixture. Next, the first mixture, which is at 80° C., is stirred in nitrogen atmosphere for 24 hours to obtain a first solution by the substitution reaction. The first solution includes first composites formed by the methoxy poly(ethylene glycol) (mPEG) and the amine-heptamethylcyanine dye. Next, the first composites in the first solution is dialyzed against 50% ethanol (ethanol: deionized water=1:1) for 5 days and then dialyzed against deionized water for 1 day to purify the first composites. Last, the solvent in the first solution is removed by lyophilization to obtain the dried first composites.

Next, 0.5 g of the first composite, 1 ml of poly(ε-caprolactone) (PCL), 10 ml of dichloromethane (DCM) and 500 μl of HCl in ether are added into a container to obtain a second mixture. Next, the second mixture, which is at 35° C., is stirred in nitrogen atmosphere for 48 hours to obtain a second solution by the polymerization reaction. The second solution includes drug carriers formed by one hydrophilic group from the methoxy poly(ethylene glycol) (mPEG), one amine-heptamethylcyanine dye and two hydrophobic groups from the poly(ε-caprolactone) (PCL). The one amine-heptamethylcyanine dye connects the one hydrophilic group from the methoxy poly(ethylene glycol) (mPEG) and the two hydrophobic groups from the poly(ε-caprolactone) (PCL), and the structure of the drug carrier is shown in formula (II). Next, the second solution is dialyzed against cold ether and then undergoes vacuum filtration to obtain the drug carriers in powder type. Next, the drug carriers is dialyzed against acetone for 5 days and then dialyzed against deionized water for 1 day to purify the drug carriers. Last, the drug carriers are dried by lyophilization.

(II)

Example 2

The manufacturing process in example 2 is similar to the manufacturing process in example 1. The difference between the manufacturing process in example 2 and example 1 are that a catalyst in a second mixture is 0.1 mg of Sn(OCt)$_2$, and the second mixture, which is at 130° C., is stirred in nitrogen atmosphere for 48 hours to obtain a second solution by the polymerization reaction.

The drug carriers of example 1 and example 2 are used for preparing nanomicelles and drug-encapsulating nanomicelles so as to undergo the following tests. When preparing the nanomicelles, the dried drug carriers are uniformly dissolved in dimethyl sulfoxide (DMSO) to obtain a drug-carrier-DMSO solution. Next, the dimethyl sulfoxide (DMSO) in the drug-carrier-DMSO solution is removed by lyophilization, and the nanomicelles formed by self-assembly of the drug carriers are left. Last, the nanomicelles are put into a phosphate buffered saline (PBS) and sonicated for 20 min; therefore, the nanomicelles are uniformly dissolved in the phosphate buffered saline (PBS) for the following tests.

When preparing the drug-encapsulating nanomicelles, the drug molecules selected to be encapsulated in the nanomicelles are Doxorubicin (Doxo). First, the dried drug carriers and Doxorubicin molecules are uniformly dissolved in dimethyl sulfoxide (DMSO) to obtain a drug-carrier-Doxorubicin-DMSO solution. Next, the dimethyl sulfoxide (DMSO) in the drug-carrier-Doxorubicin-DMSO solution is removed by lyophilization, and the drug-encapsulating nanomicelles formed by self-assembly of the drug carriers as well as Doxorubicin crystals which are not encapsulated in the drug-encapsulating nanomicelles are left. Next, the drug-encapsulating nanomicelles and the Doxorubicin crystals are separated by a sterile filter to obtain the drug-encapsulating nanomicelles. A mesh diameter of the sterile filter is 0.45 μm. Last, the drug-encapsulating nanomicelles are put into a phosphate buffered saline (PBS) and sonicated for 20 min; therefore, the drug-encapsulating nanomicelles are uniformly dissolved in the phosphate buffered saline (PBS) for the following tests.

Figure 5:
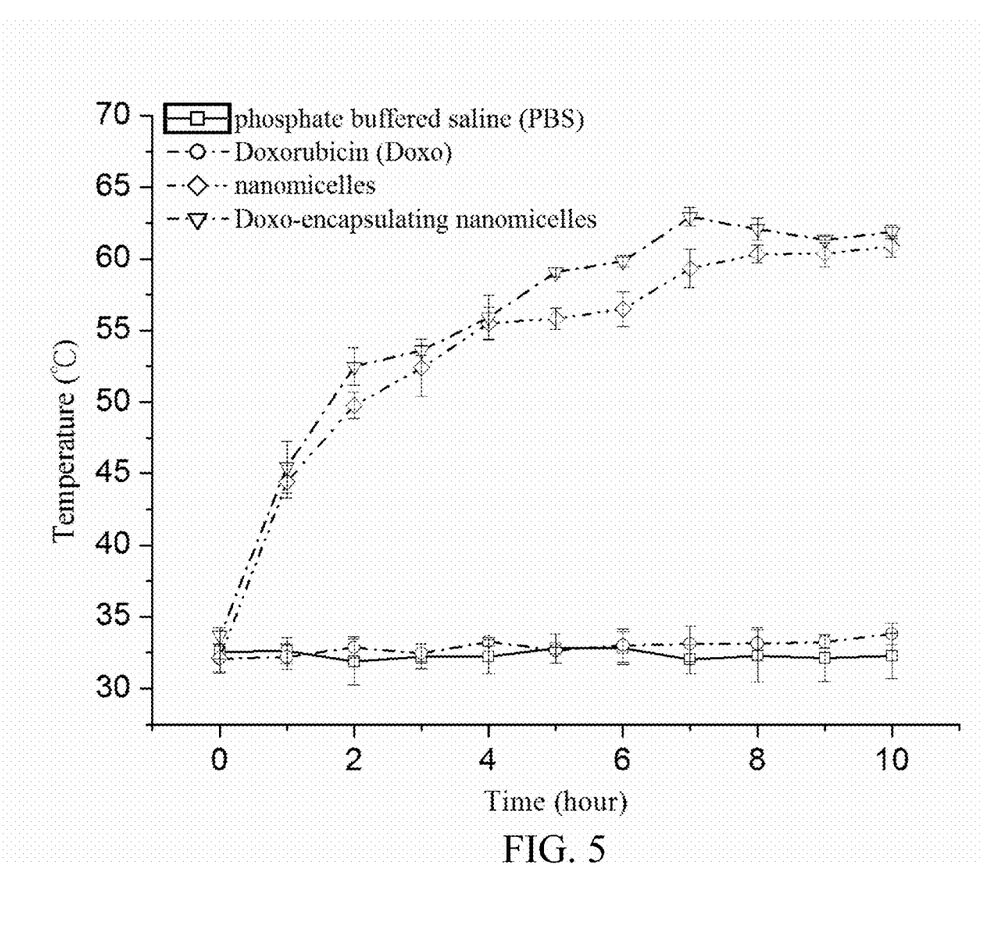
FIG. 5 is a diagram illustrating temperature variation of the nanomicelle and the drug-encapsulating nanomicelle which are irradiated by near-infrared laser according to the embodiment of the disclosure.

Please refer to FIG. 5. FIG. 5 is a diagram illustrating temperature variation of the nanomicelle and the drug-encapsulating nanomicelle which are irradiated by near-infrared laser according to the embodiment of the disclosure. When a temperature increase of samples irradiated by near-infrared light (NIR) is measured, the near-infrared light is a near-infrared laser, and the samples are the phosphate buffered saline (PBS), the Doxorubicin (Doxo), the nanomicelles and the drug-encapsulating nanomicelles which encapsulate the Doxorubicin (Doxo). A power density of the near-infrared laser is 1 W/cm$^2$, and the wavelength of the near-infrared laser is 650 nm. As shown in FIG. 5, when the irradiation time of the samples is increased, the temperatures of the nanomicelle and the drug-encapsulating nanomicelle are gradually increased. In contrast, the temperature of the phosphate buffered saline (PBS) and the Doxorubicin (Doxo) have no significant change. After being irradiated by near-infrared laser for 1 minute, the temperature of the nanomicelle and the drug-encapsulating nanomicelle are increased to 50.4° C. and 51.0° C., respectively. After being irradiated by near-infrared laser for 5 minutes, the temperatures of the nanomicelle and the drug-encapsulating nanomicelle are increased to 56.1° C. and 58.1° C., respectively. The temperatures of the nanomicelles and the drug-encapsulating nanomicelles can be increased to above 43.0° C. when irradiated by near-infrared laser and cause unrecoverable damage to the cancer cells; therefore the nanomicelles and the drug-encapsulating nanomicelles can be used for photothermal therapy of cancer.

Figure 6:
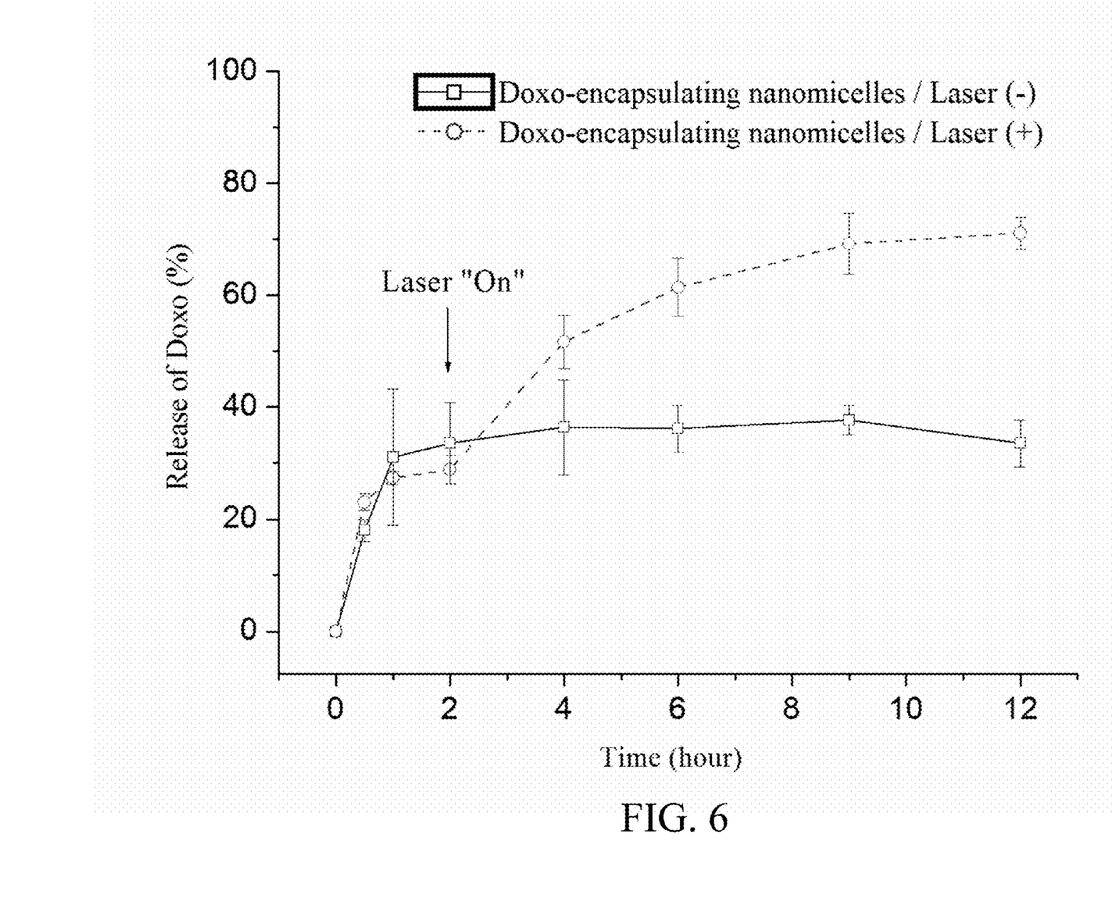
FIG. 6 is a diagram illustrating drug molecule released amount variation of the drug-encapsulating nanomicelle which are irradiated and non-irradiated by near-infrared laser according to the embodiment of the disclosure.

Please refer to FIG. 6. FIG. 6 is a diagram illustrating drug molecule released amount variation of the drug-encapsulating nanomicelle which is irradiated and non-irradiated by near-infrared laser according to the embodiment of the disclosure. When measuring a ratio of Doxorubicin (Doxo) released by the drug-encapsulating nanomicelle irradiated by near-infrared laser, a power density of the near-infrared laser is 1 W/cm$^2$, and the wavelength of the near-infrared laser is 650 nm. As shown in FIG. 6, when the irradiation time of the drug-encapsulating nanomicelle is increased, the ratio of Doxorubicin (Doxo) released by the drug-encapsulating nanomicelle is increased. After being irradiated by near-infrared laser for 10 hours, the ratio of Doxorubicin (Doxo) released by the drug-encapsulating nanomicelle is 71.3%. In contrast, the ratio of Doxorubicin (Doxo) released by the drug-encapsulating nanomicelle which is not irradiated by near-infrared laser after 10 hours is only 31.0%. When the drug-encapsulating nanomicelles is used in the cancer therapy, the ratio of the Doxorubicin (Doxo) molecules released by the drug-encapsulating nanomicelle is controlled by near-infrared laser irradiation; therefore, the Doxorubicin (Doxo) molecules encapsulated in the interior of the drug-encapsulating nanomicelles can be controlled to release around the cancer cells in the tumor so as to improve therapy efficacy.

Figure 7:
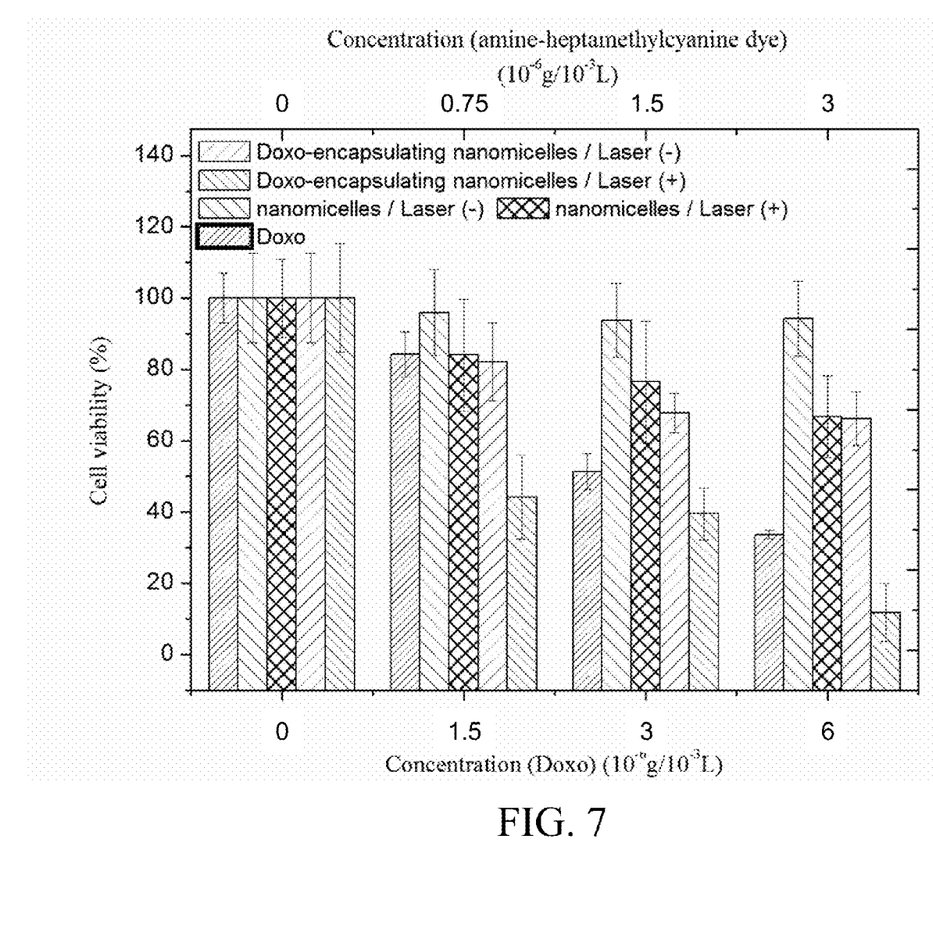
FIG. 7 is a diagram illustrating cell viability variation of cell samples treated with nanomicelles and drug-encapsulating nanomicelles which are irradiated and non-irradiated by near-infrared laser according to the embodiment of the disclosure.

Please refer to FIG. 7. FIG. 7 is a diagram illustrating cell viability variation of cell samples treated with nanomicelles and drug-encapsulating nanomicelles which are irradiated and non-irradiated by near-infrared laser according to the embodiment of the disclosure. The test of cell viability uses the drug-encapsulating nanomicelles with different Doxorubicin (Doxo) concentration as well as different amine-heptamethylcyanine dye concentration, the nanomicelles with different amine-heptamethylcyanine dye concentration and the free Doxorubicin (Doxo) with different concentration. When the drug-encapsulating nanomicelle formed with 1.5 mg/μl Doxorubicin (Doxo) and 0.75 mg/μl amine-heptamethylcyanine dye is added into a container culturing cancer cells and is irradiated by near-infrared laser, the cell viability of the cancer cell in the container is 45%. In contrast, when the drug-encapsulating nanomicelle formed by 1.5 mg/μl Doxorubicin (Doxo) and 0.75 mg/μl amine-heptamethylcyanine dye is added into a container culturing cancer cells without being irradiated by near-infrared laser, the cell viability of the cancer cell in the container is 80%. When nanomicelles with 0.75 mg/μl amine-heptamethylcyanine dye is added into a container culturing cancer cells and is irradiated by near-infrared laser, the cell viability of the cancer cell in the container is 80%. When 1.5 mg/μl Doxorubicin (Doxo) is added into a container culturing cancer cells, the cell viability of the cancer cell in the container is also 80%. Moreover, when nanomicelles with 0.75 mg/μl amine-heptamethylcyanine dye is added into a container culturing cancer cells without being irradiated by near-infrared laser, the cell viability of the cancer cell in the container is 95%.

As shown in FIG. 7, when the drug-encapsulating nanomicelles encapsulating the Doxorubicin (Doxo) molecules are irradiated by the near-infrared laser in cancer therapy, the Doxorubicin (Doxo) molecules released by the drug-encapsulating nanomicelles and the heat released by the amine-heptamethylcyanine dye in the drug-encapsulating nanomicelles for executing the photothermal therapy together generate the synergistic therapeutic effect; therefore, the number of survive cancer cells after cancer therapy by the drug-encapsulating nanomicelles is greatly reduced. As a result, the drug-encapsulating nanomicelles encapsulating the Doxorubicin (Doxo) molecules and irradiated by the near-infrared laser has better cancer therapy efficacy than the Doxorubicin (Doxo), the nanomicelles irradiated by the near-infrared laser, the nanomicelles non-irradiated by the near-infrared laser and the drug-encapsulating nanomicelles encapsulating the Doxorubicin (Doxo) molecules without irradiated by the near-infrared laser.

According to the drug carrier in the disclosure, the hydrophilic group and the hydrophobic group are connected by the organic dye so that a plurality of the drug carriers can form a nanomicelle in a polar solvent by self-assembling. The hydrophilic groups are located at the outer region of the nanomicelle, and the hydrophobic groups are located at the inner region of the nanomicelle. Therefore, the cancer drug can be encapsulated in the nanomicelle formed by the drug carriers containing organic dye. When the nanomicelle encapsulating the cancer drug arrives in the tumor through the blood vessels, the cancer drug in the nanomicelle is released inside the tumor so that high dose of the cancer drug is directly applied to the cancer cells. As a result, the amount of the normal cells directly contacted and hurt by the cancer drug during the cancer drug transporting process is reduced so that the body burden of the patients is also reduced.

Moreover, when the nanomicelles formed by the drug carriers are irradiated by near-infrared light, the organic dyes in the drug carriers emit fluorescence for generating a fluorescence image. As a result, when the living body with the nanomicelles inside is irradiated by the near-infrared light, the fluorescence emitted by the organic dyes is favorable for observing the aggregation of the nanomicelles in the living body. When the spherical nanostructures are used in cancer therapies, the location of the tumor is an area showing intense fluorescence distribution in the fluorescence image.

Moreover, when the nanomicelles formed by the drug carriers are irradiated by near-infrared light, the organic dyes in the drug carriers absorb the energy of the near-infrared light, and then temperature of the nanomicelles are raised above a photothermal therapy temperature. The photothermal therapy temperature causes irrecoverable damage on physiological functions of the cancer cells so that the cancer cells are killed.

Moreover, when the drug molecules are hydrophobic, the hydrophobic drug molecules are surrounded by the drug carriers, and then the drug carriers form the drug-encapsulating nanomicelles which encapsulate the hydrophobic drug molecules by self-assembly. Therefore, the hydrophobic drug molecules are capable for being uniformly dispersed in water in the form of being encapsulated in the drug-encapsulating nanomicelles. As a result, the hydrophobic drug molecules can be absorbed easily by living body to enter blood vessels and penetrating the blood vessels fluently to enter the tumor.

In addition, when the drug-encapsulating nanomicelles in the tumor are irradiated by the near-infrared laser in cancer therapy, the drug molecules are released by the drug-encapsulating nanomicelles. At the same time, the organic dyes absorb the near-infrared light, and then the temperature of the drug-encapsulating nanomicelles as well as the cancer cells are raised to a photothermal therapy temperature for irrecoverably damaging and killing the cancer cells. As a result, the drug molecules released by the drug-encapsulating nanomicelles and the heat released by the organic dye in the drug-encapsulating nanomicelles together generate the synergistic therapeutic effect; therefore, the number of survive cancer cells after cancer therapy by the drug-encapsulating nanomicelles is greatly reduced.

What is claimed is:

1. A drug carrier, comprising:
a hydrophilic group, a hydrophobic group and an organic dye, the hydrophilic group and the hydrophobic group being connected by the organic dye;
wherein, a plurality of the drug carriers are self-assemblable in a polar solvent to form a nanomicelle, the hydrophilic groups are located at an outer region of the nanomicelle, and the hydrophobic groups are located at an inner region of the nanomicelle;
wherein the drug carrier is represented by formula (I), wherein A is the hydrophilic group, B is the hydrophobic group, C is the organic dye, the hydrophilic group is methoxy poly(ethylene glycol) (mPEG), the hydrophobic group is poly(ε-caprolactone) (PCL), and the organic dye is heptamethine cyanine;
wherein at least one drug molecule is encapsulated in the nanomicelle;
wherein when the nanomicelle is irradiated by near-infrared light, the nanomicelle is triggered by near-infrared light and releases the at least one drug molecule.

2. The drug carrier according to claim 1, wherein the organic dye emits fluorescence when irradiated by near-infrared light.

3. The drug carrier according to claim 2, wherein when the organic dye is irradiated by near-infrared light, a temperature of the organic dye is raised to above a photothermal therapy temperature.

4. The drug carrier according to claim 3, wherein the organic dye is hydrophobic.

5. The drug carrier according to claim 1, wherein a diameter of the nanomicelle is from 20 nanometers to 300 nanometers.

6. The drug carrier according to claim 1, wherein a diameter of the nanomicelle encapsulating the at least one drug molecule is from 20 nanometers to 300 nanometers.

7. The drug carrier according to claim 1, wherein the at least one drug molecule is hydrophobic.

8. A method of manufacturing a drug carrier, comprising:
providing a first mixture, wherein the first mixture comprises a hydrophilic polymer, an organic dye and a hydrophilic organic solvent, the hydrophilic polymer comprises a hydrophilic group;
stirring the first mixture at a first temperature to obtain a first composite by a substitution reaction, wherein the first composite comprises the hydrophilic group and the organic dye which are connected with each other;
obtaining a second mixture, wherein the second mixture comprises the first composite, a hydrophobic polymer and a hydrophobic organic solvent, the hydrophobic polymer comprises a hydrophobic group;
stirring the second mixture at a second temperature to obtain a drug carrier by a polymerization reaction, wherein the drug carrier comprises the hydrophilic group, the organic dye and the hydrophobic group, the hydrophilic group and the hydrophobic group are connected by the organic dye; and mixing a plurality of the drug carriers and at least one drug molecule in a polar solvent, the at least one drug molecule encapsulated by the plurality of drug carriers to form a nanomicelle, the hydrophilic groups are located at an outer region of the nanomicelle, and the hydrophobic groups are located at an inner region of the nanomicelle;

wherein the drug carrier is represented by formula (I), (I)

wherein A is the hydrophilic group, B is the hydrophobic group, C is the organic dye, the hydrophilic group is methoxy poly(ethylene glycol) (mPEG), the hydrophobic group is poly(ε-caprolactone) (PCL), and the organic dye is heptamethine cyanine;

wherein when the nanomicelle is irradiated by near-infrared light, the nanomicelle is triggered by near-infrared light and releases the at least one drug molecular.

9. The method of manufacturing the drug carrier according to claim 8, wherein the first temperature is from 65° C. to 100° C.

10. The method of manufacturing the drug carrier according to claim 8, wherein the second mixture further comprises a catalyst, when the catalyst is HCl in ether, the second temperature is from 25° C. to 40° C.

11. The method of manufacturing the drug carrier according to claim 8, wherein the second mixture further comprises a catalyst, when the catalyst is Sn(OCt)2, the second temperature is from 110° C. to 150° C.

* * * * *